United States Patent
Meehan

(10) Patent No.: US 9,937,146 B2
(45) Date of Patent: Apr. 10, 2018

(54) ENKEPHALIN-INFLUENCING COMPOSITION AND METHOD

(71) Applicant: BIOADATP, LLC, Jackson, WY (US)

(72) Inventor: Kevin Meehan, Jackson, WY (US)

(73) Assignee: BIOADATP, LLC, Jackson, WY (US)

( * ) Notice: Subject to any disclaimer, the term of this patent is extended or adjusted under 35 U.S.C. 154(b) by 0 days.

(21) Appl. No.: 15/078,485

(22) Filed: Mar. 23, 2016

(65) Prior Publication Data

US 2017/0273937 A1 Sep. 28, 2017

(51) Int. Cl.
| | |
|---|---|
| *A61K 31/198* | (2006.01) |
| *A61K 31/352* | (2006.01) |
| *A61K 31/197* | (2006.01) |
| *A61K 31/675* | (2006.01) |

(52) U.S. Cl.
CPC .......... *A61K 31/352* (2013.01); *A61K 31/197* (2013.01); *A61K 31/198* (2013.01); *A61K 31/675* (2013.01)

(58) Field of Classification Search
CPC ............................ A61K 31/352; A61K 31/675
See application file for complete search history.

(56) References Cited

U.S. PATENT DOCUMENTS

| | | | |
|---|---|---|---|
| 6,159,506 A | 12/2000 | Bieser et al. | |
| 6,949,582 B1 * | 9/2005 | Wallace | A61K 31/05 514/454 |
| 7,255,882 B2 | 8/2007 | Bieser et al. | |
| 8,012,924 B2 * | 9/2011 | Abe | A61K 31/198 514/1.1 |
| 8,633,150 B2 | 1/2014 | Plotnikoff | |
| 2002/0122835 A1 * | 9/2002 | Bucci | A61K 31/198 424/729 |
| 2004/0110828 A1 | 6/2004 | Chowdhury et al. | |
| 2004/0116351 A1 | 6/2004 | Halevie-Goldman | |
| 2004/0241256 A1 * | 12/2004 | Ehrenpreis | A61K 31/737 424/734 |
| 2007/0286909 A1 | 12/2007 | Smith et al. | |
| 2008/0031869 A1 | 2/2008 | Fontaine | |
| 2011/0081329 A1 * | 4/2011 | Smith | A61K 31/198 424/94.1 |
| 2011/0189161 A1 | 8/2011 | Blum et al. | |
| 2013/0252924 A1 | 9/2013 | Penninger et al. | |

FOREIGN PATENT DOCUMENTS

WO 2000/041686 A1 7/2000

OTHER PUBLICATIONS

International Search Report for PCT Application No. PCT/US2017/023896, dated Jun. 7, 2017, 3 pages.

* cited by examiner

*Primary Examiner* — San-Ming Hui
(74) *Attorney, Agent, or Firm* — Marger Johnson

(57) ABSTRACT

A composition which includes Phenylalanine, Serine, Glutamine and GABA (γ-aminobutyric acid). The composition contains the essential amino acids Phenylalanine; Glutamine; the non-essential amino acid Serine; and GABA (γ-aminobutyric acid) in concentrations effective to influence or modulate the neurotransmitter pentapeptide enkephalin. The composition may further comprise tetrahydrocannabinol (THC).

17 Claims, No Drawings

ENKEPHALIN-INFLUENCING COMPOSITION AND METHOD

TECHNICAL FIELD

This disclosure generally relates to a composition and method for influencing pain management. More particularly, this disclosure relates to a composition and method formulated to influence the enkephalins.

BACKGROUND

The use of marijuana for medicinal and recreational purposes is on the rise among the general population. Along with the rise of use, state laws are now changing to reflect the evolving attitude of the American public. As of early 2016, five jurisdictions have legalized the recreational use of marijuana—Washington, Colorado, Oregon, Alaska, and Washington, D.C. Many more states now allow the medicinal use of marijuana—Alaska, Arizona, California, Colorado, Connecticut, Washington, D.C., Delaware, Hawaii, Illinois, Maine, Maryland, Massachusetts, Michigan, Minnesota, Montana, Nevada, New Hampshire, New Jersey, New Mexico, New York, Oregon, Rhode Island, Vermont, and Washington.

The least contentious use of marijuana is for medicinal purposes. Marijuana has been recognized as an effective treatment for many medical conditions, including but not limited to cancer, anorexia, AIDS, chronic pain, cachexia, persistent muscle spasms, multiple sclerosis, seizures, epilepsy, severe nausea, glaucoma, arthritis, migraine, and Any other chronic or persistent medical symptom that substantially limits the ability of the person to conduct one or more major life activities (as defined by the Americans with Disabilities Act of 1990) or, if not alleviated, may cause serious harm to the patient's safety or physical or mental health. The recognized conditions vary by state. However, most jurisdictions permit the use of marijuana for pain management.

There are over 480 natural components found in Cannabis, which include delta-9-tetrahydrocannabinol (commonly referred to as THC) and cannabinoids. Cannabidiol (CBD), cannabinol (CBN), cannabadivarin (THCU), cannabigerol (CBG), cannabichromene (CBC), cannabicyclol (CBL), cannabitriol (CBT), and cannabiscoin (CBE) are some of the many cannabinoids found in the Cannabis plant. Each cannabinoid is structurally similar but differentiated by its interaction with the user's central nervous system receptors. THC is the most well-known component found in marijuana. Many of these components have been studied for its physiological impact on the human body and thus potential use for medical purposes.

The use of tetrahydrocannabinol (THC) and cannabichromene (CBC) in the management of pain has been well documented. THC is a chemical which binds to the specific receptor site; cannabinoid receptor CB1 and CB2. While it is not completely known how THC and CBC alleviate pain, many studies have hypothesized multi-level, non-competitive direct and indirect interaction of the cannabinoid and opioid receptor systems.

Enkephalin is one of three well-defined endogenous opioid peptides found in the body, the other two being—endorphins and dynorphins. These substances are known to have potent painkilling properties. Endogenous opioid peptides act as neuromodulators that modify the actions of other neurotransmitters in the central nervous system. The inventor recognizes enkephalin's role in regulating nociception, the ability for the body to interpret harmful stimuli. Enkephalins are internally propagated and bind to the body's opioid receptors.

The opioid receptors, mu receptors (MOR) and delta receptors (DOR), contain enkephalins as its binding site protein. The opioid receptors discussed herein are recognized for their analgesic potential and mood modulating roles. It is further recognized that the DOR modulates the nociception of chronic pain whereas the MOR modulates acute pain. Enkephalins are the endogenous ligands which bind to the mentioned opiate receptors described herein. The inventor recognizes that the two forms of enkephalins (Met-enkephalin and Leu-enkephalin) contain the amino acids, Methionine (Met) and Leucine (Leu).

In addition to THC and its interaction with the opioid receptor system, phenylalanine is recognized as an analgesic. Phenylalanine's role as an analgesic is best postulated by its blockage of enkephalin degradation. Phenylalanine has demonstrated to produce naloxone reversible analgesia and consequently increase the analgesic properties of enkephalins. Phenylalanine is the primary precursor for dopamine. The inventor recognizes the role of dopaminergic neurotransmission as a natural analgesic within the supraspinal regions and the role of dopamines descending inhibition of pain. Decreased levels of dopamine levels are probable for increased pain signaling in many animal conditions.

Serine's role participates in the phosphorylation of serine containing analogs and has been recognized to potentiate the blood brain barrier permeability and CNS bioavailability of peptides. This process assists in the biochemical delivery platform of the composition.

Glutamine is one of the few amino acids capable of penetrating the blood brain barrier. Glutamine biosynthesizes glutamate and hence has a two-fold purpose in the composition. It serves in the biosynthesis of γ-aminobutyric acid. Increasing the blood brain barrier penetrating mechanism presents a higher efficacy potential for increased rates of GABA, THC and CBC within the RAIC.

GABA (γ-aminobutyric acid) plays a chief role in reducing neuronal excitability in the nervous system. It is synthesized from glutamate via GAD reaction. It has been demonstrated that the cerebral cortex partakes in the role of regulating pain. When GABA levels are increased in the small region of the cerebral cortex and the rostral angular insular cortex (RAIC), the animal(s) displayed increased and consistent analgesia. This suggests that GABA may function in part to enhance the inhibition of the neurons which illicit pain. By utilizing Glutamine/ Glutamate in conjunction with GABA, the potentiating effect on the RAIC is heightened.

The inventor has recognized that the reduction of pain may be enhanced in animals by utilizing the composition which contains the amino acid Phenylalanine, Serine, Glutamine, GABA, and optionally THC, in an ingestible form, and optionally other enumerated components. The organizational blueprint of the claimed composition is designed to biochemically synergize each individual component to elicit a higher rate of efficacy of the enkephalins.

DETAILED DESCRIPTION OF EXEMPLARY EMBODIMENTS

Since the understood increase in enkephalin activity and the descending pathways of antinociception creates analgesia and diminishment in neuralgia, the inventor has found that it would be advantageous to develop formulations which increase the allosteric modulating effect of both μ and δ-opioid receptors, increase enkephalin activity and stimulate descending pathways of antinociception. The disclosure relates to a composition which increases the activity of the naturally-occurring peptide, enkephalin, found in animals. Enkephalins (and beta-endorphins) are recognized as endogenous opioids.

The composition presented here is proposed to act as an allosteric modulator, alone or in conjunction with THC, of the μ and δ-opioid receptors, which is one of the biochemical destinies of THC. The inventor has recognized that THC and CBC stimulates descending biochemical pathways of antinociception, creating the analgesia effect noted and therefore presents the composition as an isolated component or in conjunction with THC, CBC or the natural cannabinoid group in enhancing this stimulatory effect which reduces pain and inflammation.

The composition contains the essential amino acids phenylalanine; glutamine; the non-essential amino acid serine; GABA (γ-aminobutyric acid); and optionally THC, in concentrations effective to influence or modulate the neurotransmitter pentapeptide enkephalin. Another component, Tyrosine, is synthesized from phenylalanine and converted to L-DOPA which is the precursor to the neurotransmitter dopamine. It is recognized that increasing the gradient of dopamine in the synaptic cleft, increases the antinociception. Further, Threonine and serine kinase encoding appears to modulate TOA3, which indicates pain relieving properties. This directive incorporates pain reducing potentiality.

This composition can be introduced with or without the component of THC, CBD, CBC, CBN, CBG or any of the other molecules which make up the phytocannabinoid family. The biochemical effects of the composition and each component in the arrangement described are included in the descriptive embodiments. Most of the single components within the arrangement induce a synergistic effect on each of the other components within the composition, in particular on THC, when introduced into the mammal.

According to some embodiments, the active component of the composition includes ingredients such as phenylalanine, glutamine, serine, and GABA (γ-aminobutyric acid). In one embodiments, the active component of the composition consists essentially of phenylalanine, glutamine, serine, GABA, and THC. In another embodiment, the active components consist essentially of phenylalanine, glutamine, serine, GABA, and at least one of the following components: glutamate, threonine, tyrosine, leucine, methionine, and pyridoxal-5-phosphate. In yet another embodiment, the active components include phenylalanine, glutamine, serine, GABA, THC, and at least one of the following components: glutamate, threonine, tyrosine, leucine, methionine, and pyridoxal-5-phosphate.

Acceptable excipients for the composition include but are not limited to Methionine and Leucine. These components may exist as dextrorotation, levorotation, or a mix of both. The range of Methionine may vary from 0.01% of the total composition without an upper limit. Leucine may also be present from 0.01% of the total composition and no upper limit. Further, acceptable solvents include but are not limited to liquid or metal states, including salts.

Table 1A lists some of the ingredients in an ingestible composition according to some exemplary embodiments of the invention as well as the exemplary concentration ranges for those ingredients. As shown in Table 1A, the ingestible composition may optionally include the amino acids Threonine, Tyrosine, Methionine and Leucine and the co-factor Pyridoxyl-5-Phosphate (B-6) or any combination thereof.

The amount of the ingredients are given in concentration range or percentage by weight of the ingredient in the total composition.

TABLE 1A

| Component | Concentration Range (mcgs) |
| --- | --- |
| Phenylalanine | from 0.1 |
| Serine | from 0.1 |
| Glutamine | from 0.1 |
| GABA | from 0.1 |
| Glutamate (Glutamic Acid, (optional)) | from 0.1 to 300 |
| THC (optional) | From 0.0001 |
| Threonine (optional) | from 1.0 |
| Tyrosine (optional) | from 0.1 |
| Leucine (optional) | from 0.1 |
| Methionine (optional) | from 1.0 |
| Pyridoxal-5-Phosphate (optional) | from 1.0 |

As shown in Table 1A, the ingestible composition includes, at a minimum 1 mcg (or about 1 mcg) of Phenylalanine, 1 mcg (or about 1 mcg) of Serine, 1 mcg (or about 1 mcg) of Glutamine and 1 mcg (or about 1 mcg) of GABA (γ-aminobutyric acid). There is no upper limit on the concentration ranges of the following components: Phenylalanine, Serine, Glutamine and GABA (γ-aminobutyric acid). The concentration of THC is between 0.0001 to no upper limit.

In one embodiment, there is no upper limit to the amounts listed for any of the ingredients listed in Table 1A with the exception of the optional ingredient, glutamate. As one skilled in the art would understand, the concentration range should be as high as a carrier will tolerate, which may be a one hundred percent composition and no solvent to the other extreme of broadening it to as low as a one-to-one ratio. Furthermore, as noted in the description and table, not all of the ingredients of Table 1A need to be used in the composition. For example, in one embodiment, the composition may include only phenylalanine, serine, glutamine, GABA, and glutamate. In yet another embodiment, the active ingredients are comprised of phenylalanine, serine, glutamine, GABA, and methionine.

An exemplary ingestible composition according to an exemplary embodiment of the invention includes the ingredients listed in Table 2A. The amount of the ingredients is given in milligrams per one dose of the composition.

TABLE 2A

| Component | Concentration Range (mcgs) |
| --- | --- |
| Phenylalanine | 50.0 |
| Serine | 1.0 |
| Glutamine | 5.0 |
| GABA | 35.0 |
| THC (optional) | 0.0001 |
| Glutamate (Glutamic Acid, (optional)) | 5.0 |
| Threonine (optional) | 0.5 |
| Tyrosine (optional) | 0.5 |
| Leucine (optional) | 1 |
| Methionine (optional) | 1 |
| Pyridoxal-5-Phosphate (optional) | 1 |

In one embodiment, as shown in Table 2A, all components are present in the composition. The composition is comprised of phenylalanine, serine, glutamine, GABA, THC, Glutamate, Threonine, Tyrosine, Leucine, Methionine, and Pyridoxal-5-Phosphate. Phenylalanine is the most abundant active ingredient in the composition with the concentration range of 50% of the total composition. Serine is exemplary present in the amount of concentration range of 1.0%.

In yet another exemplary embodiment, the active ingredients—phenylalanine, serine, glutamine, GABA—are present in the composition with decreasing weight percentages. Phenylalanine is present as the most abundant of the active ingredients in the composition. The concentration range of GABA present in the composition is less than the concentration range of phenylalanine. The concentration range of glutamine present in the composition is less than the concentration of GABA. The concentration range of serine present in the composition is less than the concentration of glutamine.

The above descriptions are merely some examples of concentrations and capabilities available. No limitation to any particular embodiment is intended nor should be implied. Different processes may be separated and/or combined differently within the scope of embodiments.

The basic principles of producing or compounding this composition can be followed in a variety of methods; utilizing different mediums as solvents for the solution; powder, granular or liquid. The final composition may be a capsule, compressed tablet, or a solution in a liquid solvent medium. The composition may be ingested in any deliverable form to a mammal.

It will be appreciated that several of the above-disclosed and other features and functions, or alternatives thereof, may be desirably combined into may other different compositions, applications, and methods. Also that various presently unforeseen or unanticipated alternatives, modifications, variations, or improvements therein may be subsequently made by those skilled in the art which are also intended to be encompassed by the embodiments here.

While this invention has been particularly shown and described with reference to exemplary embodiments thereof, it will be understood by those skilled in the art that various changes in form and details may be made therein without departing from the spirit and scope of the embodiments described therein.

The invention claimed is:

1. A composition comprising:
    a plurality of active ingredients comprising:
        phenylalanine;
        serine;
        glutamine;
        γ-aminobutyric acid; and
        tetrahydrocannabinol.

2. The composition of claim 1, further comprising at least one of threonine, tyrosine, leucine, methionine, and glutamate.

3. The composition of claim 1, further compromising pyridoxal-5-phosphate.

4. The composition of claim 1, wherein a proportion by weight of phenylalanine is at least about 0.1%.

5. The composition of claim 1, wherein a proportion by weight of serine is at least about 0.1%.

6. The composition of claim 1, wherein a proportion by weight of glutamine is at least about 0.1%.

7. The composition of claim 1, wherein a proportion by weight of γ-aminobutyric acid is at least about 0.1%.

8. The composition of claim 1, wherein a proportion by weight of tetrahydrocannabinol is at least about 0.0001%.

9. The composition of claim 2, wherein a proportion by weight of threonine is at least about 1.0%.

10. The composition of claim 2, wherein a proportion by weight of tyrosine is at least about 0.1%.

11. The composition of claim 2, wherein a proportion by weight of leucine is at least about 0.1%.

12. The composition of claim 2, wherein a proportion by weight of methionine is at least about 1.0%.

13. The composition of claim 3, wherein a proportion by weight of pyridoxal-5-phosphate is at least about 1.0%.

14. The composition of claim 2, wherein a proportion by weight of glutamate is at least about 0.1%.

15. The composition of claim 1, wherein a proportion by weight of the active ingredients comprises:
    about 50.0% phenylalanine;
    about 1.0% serine;
    about 5.0% glutamine; and
    about 35.0% γ-aminobutyric acid.

16. The composition of claim 1, wherein a proportion by weight of phenylalanine is at least about 20%.

17. The composition of claim 1, wherein:
    a proportion by weight of serine is less than a proportion by weight of glutamine;
    the proportion by weight of glutamine is less than a proportion by weight of γ-aminobutyric acid; and
    the proportion by weight of γ-aminobutyric acid is less than a proportion by weight of phenylalanine.

* * * * *